(12) United States Patent
Yamatsu et al.

(10) Patent No.: US 7,709,248 B2
(45) Date of Patent: May 4, 2010

(54) BIOASSAY UNIT AND SUBSTRATE FOR BIOASSAY

(75) Inventors: Hisayuki Yamatsu, Tokyo (JP); Motohiro Furuki, Tokyo (JP); Masanobu Yamamoto, Kanagawa (JP)

(73) Assignee: Sony Corporation, Tokyo (JP)

( * ) Notice: Subject to any disclaimer, the term of this patent is extended or adjusted under 35 U.S.C. 154(b) by 1005 days.

(21) Appl. No.: 10/486,022

(22) PCT Filed: May 30, 2003

(86) PCT No.: PCT/JP03/06814

§ 371 (c)(1), (2), (4) Date: Sep. 16, 2004

(87) PCT Pub. No.: WO03/104805

PCT Pub. Date: Dec. 18, 2003

(65) Prior Publication Data

US 2005/0048595 A1 Mar. 3, 2005

(30) Foreign Application Priority Data

Jun. 6, 2002 (JP) .............................. 2002-165457

(51) Int. Cl.
*G01N 33/53* (2006.01)
*C12Q 1/00* (2006.01)
*C12Q 1/68* (2006.01)

(52) U.S. Cl. .................. 435/287.2; 435/6; 435/7.1; 435/91.1; 435/91.2; 356/123; 356/244

(58) Field of Classification Search ................. None
See application file for complete search history.

(56) References Cited

U.S. PATENT DOCUMENTS 5,143,854 A * 9/1992 Pirrung et al. .............. 436/518

(Continued)

FOREIGN PATENT DOCUMENTS

EP 0 886 141 12/1998

(Continued)

OTHER PUBLICATIONS

Supplementary European Search Report, issued on Dec. 21, 2007, from the European Patent Office in counterpart European Patent Application No. 03-73-0709.

(Continued)

*Primary Examiner*—Jill Warden
*Assistant Examiner*—Timothy G Kingan
(74) *Attorney, Agent, or Firm*—Finnegan, Henderson, Farabow, Garrett & Dunner, L.L.P.

(57) ABSTRACT

To provide a bioassay system or the like, which can solve the problem of allocating spaces above detecting sections and can also stabilize servo-controlled operation of a disk-shaped plate.

Provided is a bioassay system (U) or the like, which is equipped with at least means for immobilizing a nucleotide chain, a peptide, a protein, a lipid, a low molecular-weight compound, a liposome or any other biological substance as a detection substance (D) in a detecting section (3), dropping a target-substance containing solution (S) onto the immobilized detection substance (D), and causing the detection substance (D) and the target substance (T) to interact with each other to prepare a reaction product (R); and means for condensing fluorescence (F), which has been emitted from the fluorescence-labeled substance (D) by irradiating excitation light (P) of a specific wavelength onto the reaction product (R), by a lens (5) arranged on a side of a back surface (102) of the reaction section (3) to determine an intensity of the fluorescence (F).

12 Claims, 6 Drawing Sheets

U.S. PATENT DOCUMENTS

| | | | |
|---|---|---|---|
| 5,333,675 A * | 8/1994 | Mullis et al. | 165/268 |
| 6,013,513 A | 1/2000 | Reber et al. | |
| 6,117,630 A | 9/2000 | Reber et al. | |
| 6,160,787 A * | 12/2000 | Marquardt et al. | 369/275.1 |
| 6,537,801 B1 * | 3/2003 | Ida et al. | 435/287.2 |
| 2004/0021867 A1 * | 2/2004 | Karthe et al. | 356/417 |
| 2005/0014286 A1 | 1/2005 | Furuki et al. | |

FOREIGN PATENT DOCUMENTS

| | | | |
|---|---|---|---|
| JP | 04-315947 | * | 6/1992 |
| JP | 4-315947 | | 11/1992 |
| JP | U04-315947 | * | 11/1992 |
| JP | 2001-238674 | | 9/2001 |
| JP | 2002-501174 | | 1/2002 |
| WO | WO 00/06198 | | 2/2000 |
| WO | WO 00/20861 | | 4/2000 |
| WO | WO-03/079013 | | 9/2003 |

OTHER PUBLICATIONS

Communication issued from the European Patent Office on Jan. 12, 2009 in counterpart European Patent Application No. 03730709.7.

* cited by examiner

BIOASSAY UNIT AND SUBSTRATE FOR BIOASSAY

TECHNICAL FIELD

This invention relates to a bioassay system useful in the field of bioinformatics. More specifically, the present invention is concerned with a bioassay system devised such that fluorescence emitted from a fluorescence-labeled substance existing in a detecting section of prescribed construction is condensed on a back side of the detecting section to determine an intensity of the fluorescence.

BACKGROUND ART

Nowadays, molecule-integrated bioassay substrates with predetermined DNAs finely arrayed thereon by microarray techniques, which are generally called DNA chips or DNA microarrays (hereinafter collectively called "DNA chips"), are used in mutation analyses of genes, SNPs (single-base polymorphisms) analyses, gene expression frequency analyses, and the like, and have begun to find utility in a wide variety of fields such as drug developments, clinical diagnoses, pharmacogenomics and forensic medicine.

This DNA chip is characterized in that it permits a comprehensive analysis of intermolecular reactions such as hybridizations, because a wide variety of numerous DNA oligosaccharide chains, cDNAs (complementary DNAs) or the like are integrated on a glass substrate or silicon substrate.

An illustrative analytical procedure by a DNA chip will be described briefly. To a DNA probe immobilized on a glass substrate or silicon substrate, hybridization is performed on the substrate by subjecting mRNA, which has been extracted from cells, a tissue or the like, to PCR amplification in the presence of a fluorescence-labeled dNTP by reverse transcriptase PCR reaction or the like while integrating the fluorescence-labeled dNTP as a fluorescent probe. Fluorometry is then performed with a prescribed detector.

With a view to achieving an increase in the number of target substances to be handled and improvements in detection accuracy and detection speed in a bioassay method making use of the above-described DNA chip, substrate techniques and servo control techniques fostered in connection with optical disks can be proposed.

Described specifically, a solution with a detection substance contained therein is dropped to a predetermined position on a substrate while rotating the same, and is immobilized on the substrate. With the substrate kept rotating, a solution with a fluorescence-labeled target substance contained therein is then dropped onto the immobilized detection substance to cause the detection substance and the target substance to interact with each other, and the target substance not contributed to the interaction is washed off. With the substrate kept in rotation, excitation light is subsequently irradiated onto the interacted target substance, fluorescence emitted from the fluorescent label is detected by a detector, and an intensity of the fluorescence so detected is determined to analyze the binding strength between the detection substance and the target substance (see, for example, JP 2001-238674 A).

The above-described bioassay method making use of a substrate (hereinafter called "disk assay" for the sake of convenience in description) has a merit in that compared with the conventional one called "DNA chip", a huge number of detection substances and target substances can be very economically arrayed on a substrate by making use of injection molding techniques, which are employed in the preparation of substrates for optical disks, and surface microprocessing techniques.

Further, it is possible to achieve an improvement in detection speed by rotating a substrate at a high speed and performing fluorometric detections with a high-sensitivity detector. There is a further merit in that, if samples of a target substance carried at a high degree of integration on a substrate as described above are repeatedly analyzed by a high-speed assay system, the results can be statistically processed to achieve an improvement in detection accuracy.

In the above-described disk assay, however, a sample solution is dropped downwardly from a point above a substrate, which is held in a horizontal position, onto predetermined detecting sections (spot regions). Accordingly, a dropper (for example, an inkjet printing apparatus) is arranged above the substrate. If a construction is adopted such that a detection unit is arranged above the substrate for the detection of the intensity of fluorescence emitted from each fluorescence-labeled target substance, a problem therefore arises in the allocation of spaces for the dropper group and the detection unit, leading to a technical problem that the arrangement of the dropper group becomes complex. Under the current circumstance that the move toward more complex droppers equipped with a greater number of nozzles is expected to advance further, it is crucial to solve the above-described technical problem.

In a disk assay, it is important to assure fail-free operations of a focusing servo control system, which serves to maintain constant the distance between the substrate and a condenser lens, and a tracking servo control system, which serves to cause a fluorescence condenser lens to track detection substances and target substances arrayed on the substrate, so that effects of dynamic disturbances caused by eccentricity and warpage of the substrate can be reduced.

Servo control information (a servo error signal), which is required to operate these servo control systems, are obtained by irradiating a laser beam onto a surface of the disk through the condenser lens and optically and electrically processing the laser beam reflected back to the condenser lens. On the surface of the substrate, however, the detection substance and the target substance are unevenly present from the optical viewpoint. Therefore, the reflected laser beam returned as a result of upward reflection of the laser beam irradiated from a side above the substrate has been subjected to scattering. As a consequence, the servo error signal includes a large noise, developing a technical problem that the operations of the servo control systems are rendered unstable.

A primary object of the present invention is, therefore, to solve the problem in allocating spaces above the detection unit and specifically, to provide a bioassay system which can stabilize servo-controlled operations with respect to a substrate.

DISCLOSURE OF INVENTION

To solve the above-described technical problems, the present invention provides the following bioassay system and bioassay substrate.

Firstly, the present application provides a bioassay system devised to include means for dropping a solution of a fluorescence-labeled target substance onto a detection substance (for example, a nucleotide chain, a peptide, a protein, a lipid, a low molecular-weight compound, a liposome, or any other biological substance or the like) existing in a reaction region and causing the detection substance and the target substance to interact with each other in the reaction region to prepare a reaction product; and means for irradiating excitation light of a specific wavelength onto the reaction product and condensing fluorescence, which has been emitted from the fluorescence-labeled substance, on a back side of the reaction region to determine an intensity of the fluorescence.

The bioassay system is devised to arrange the fluorescence-intensity determining means on the back side of the reaction region in a detecting section, so that a wider space can be retained above the detecting section. As a consequence, a merit has been brought about in that a device for dropping a sample solution and a group of devices associated with the dropping device can be arranged with a higher designing tolerance.

In the system, excitation-light irradiating means for obtaining fluorescence may be arranged either above (on a front side of) or below (on a back side of) the detecting section. It is, however, suitable to arrange the excitation-light irradiating means together with the fluorescence-intensity determining means on the back side of the detecting section, because a still wider space can be formed above the detecting section.

Specifically, the system can be constructed such that a light transmitting layer having translucence to the fluorescence emitted from the fluorescence-labeled target substance is formed at least in the detecting section and excitation light is irradiated toward the detection substance, which exists in the reaction region, from a back side of the detecting section. By devising the system such that the intensity of the fluorescence returning to the back side through the light transmitting layer is determined, both of the excitation-light irradiating means and the fluorescence-intensity determining means can be arranged on the back side of the detecting section.

Secondly, the present application also provides a bioassay substrate of a construction that a detecting section provided with at least a reaction region, which provides a place of an interaction between a detection substance and a target substance, is arranged and a light transmitting layer having translucence to both of excitation light and fluorescence is formed on a bottom wall of the reaction region in the detecting section. Incidentally, fluorescence may be obtained using a fluorescent intercalator.

This "bioassay substrate" makes it possible to irradiate excitation light from a back side of a detecting section arranged on the substrate and to condense fluorescence, which has been obtained from the detecting section by the irradiation, on the back side of the detecting section to determine the intensity of the fluorescence. Accordingly, a wider space can be obtained above the substrate. As a consequence, a device for dropping a sample solution and a group of devices associated with the dropping device can be arranged with a higher designing tolerance.

The above-described bioassay substrate can be devised such that a substrate constructed to optically furnish position information and focus information on each detecting section arranged on a substrate is adopted and the light transmitting layer arranged in the detecting section is caused to function as a reflecting layer provided with property of causing reflection of a laser beam. Namely, this light transmitting layer has translucence to both of the excitation light and fluorescence, and also, a function to reflect a laser beam.

The above-described bioassay substrate according to the present invention can also be devised such that a substrate of the above-described construction is used and an assay is performed using detecting sections arranged on the substrate.

When the substrate constructed to optically furnish the position information and focus information on each detecting section is used, it is necessary to assure fail-free operations of a focusing servo control system, which serves to maintain constant the distance between the substrate and a condenser lens, and a tracking servo control system, which serves to cause a fluorescence condenser lens to track detection substances and target substances arrayed on the substrate, so that effects of dynamic disturbances caused by eccentricity and warpage of the substrate can be reduced.

As described above, the light transmitting layer formed in each detecting section arranged on the substrate has translucence to both of the excitation light and fluorescence, and also laser-beam-reflecting ability. It is, therefore, possible to condense a laser beam through a lens arranged on the back side (on the side of the surface opposite to the surface in which the detecting sections are formed) of the substrate and to irradiate the thus-condensed laser beam onto the reflecting layer, to obtain focus information from the laser beam reflected back from the reflecting layer, and by using the focus information, to operate the focus servo control system to maintain constant the distance between the lens and the substrate.

Further, tracking information can be obtained by condensing a laser beam through the lens arranged on the side of the surface opposite to the front surface of the substrate, irradiating the thus-condensed laser bean onto the reflecting layer and using the reflected laser beam reflected back from the reflecting layer. Use of this tracking information makes it possible to operate the tracking servo control system such that the lens is allowed to accurately track the array of the detecting sections.

The above-described servo control related means equipped with the basic construction, which irradiates a laser beam from the side of the back surface of the substrate and obtains a reflected laser beam on the side of the back surface, can eliminate scattering of the reflected laser beam, which would otherwise occur under the influence of detection substance and target substance considered to unevenly exist on the surface of the substrate from the optical viewpoint. It is, therefore, possible to eliminate noises from servo error signals and to stabilize the servo controlled operation.

In the bioassay system of the above-described construction, excitation light irradiated onto the substrate to induce emission of fluorescence from the fluorescence-labeled target substance can also be used as a laser beam for performing the above-described servo controlled operation, and vice versa. According to this embodiment, the optical system arranged around the substrate can be further simplified in construction, thereby making it possible to promote the cost reduction, size reduction and the like of the system.

In the above-described bioassay system, the bioassay substrate can be held with its front surface facing vertically upward, in other words, can be held horizontally. This makes it possible to accurately perform dropping of a sample solution to each of predetermined detecting sections in the direction of gravity, and further, to drop of small droplets of a uniform size and shape to the individual detecting sections. Therefore, the accuracy of fluorometric detection can be improved.

As has been described in the above, the bioassay system according to the present invention has the technical significance that it provides the relevant business field with a technique to solve the problem in allocating spaces for the sample solution dropper and the fluorescence intensity determination unit and, when the substrate is adopted, also with a technique to reduce noises in servo error signals and to permit stabilization of serve-controlled operations (servo control of focusing and servo control of tracking).

BEST MODES FOR CARRYING OUT THE INVENTION

Figure 1:
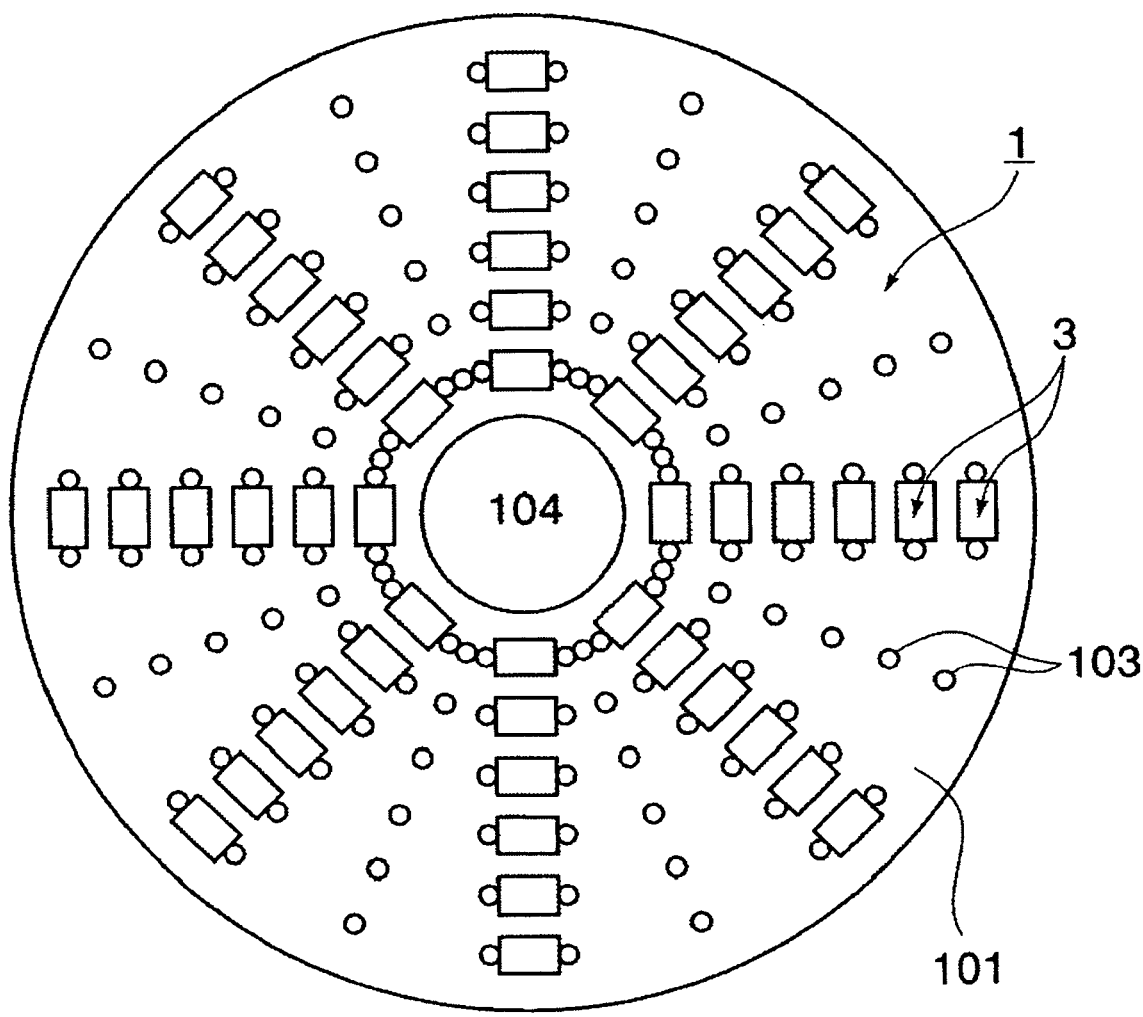
FIG. 1 is a top plan view of a substrate (1) suited for use on a bioassay system according to the present invention.
Figure 2:
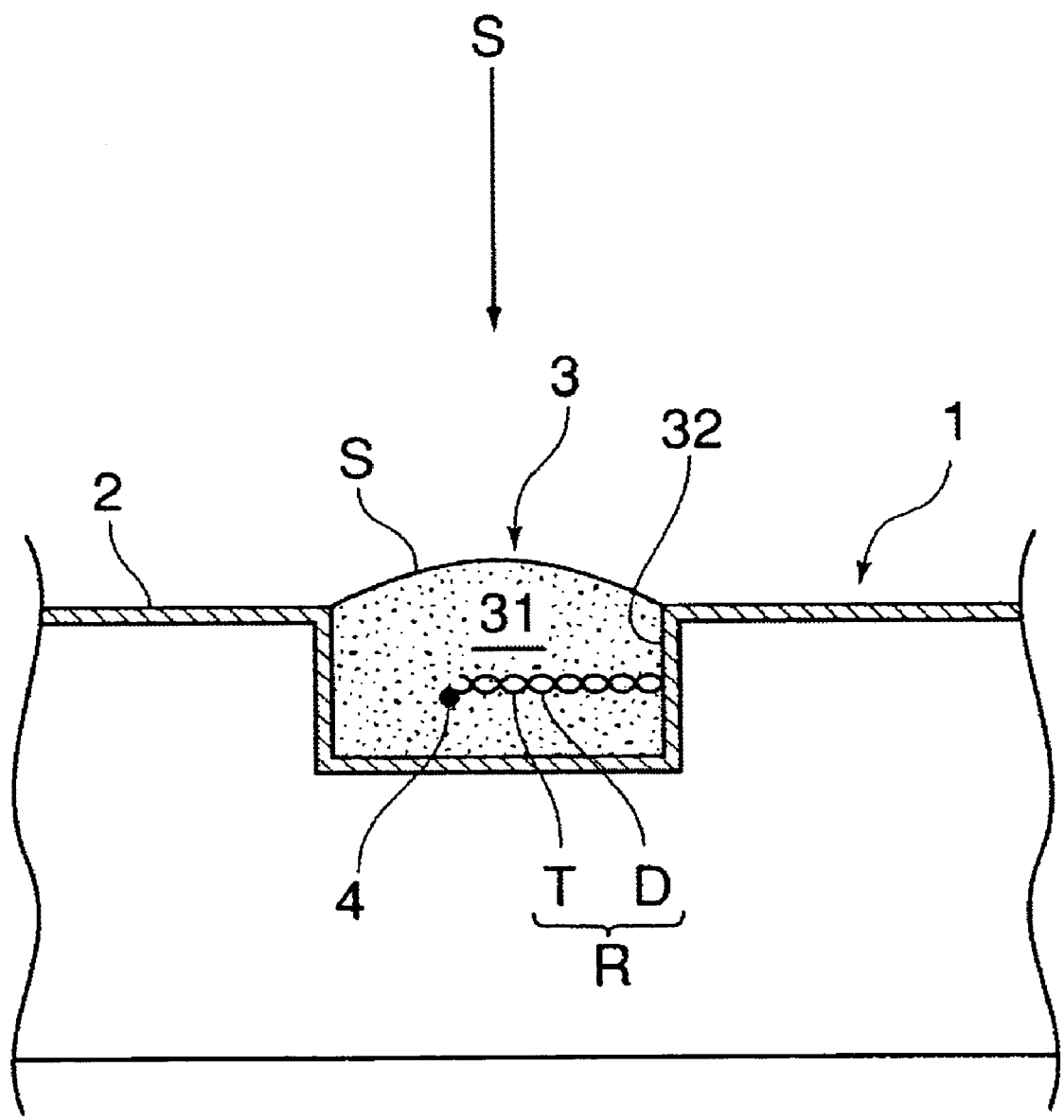
FIG. 2 is an enlarged fragmentary view of a detecting section (3) arranged on the substrate (1) and its surrounding area.

With reference to the accompanying drawings, a description will hereinafter be made about the construction of the bioassay system according to the present invention. FIG. 1 is a top plan view of a bioassay substrate according to the present invention, which is suited for use on the bioassay system, and FIG. 2 is a schematic view of a detecting section arranged on the substrate and its surrounding area.

A substrate designated at numeral 1 in FIG. 1 is formed of a material which is adopted for substrates (disks) employed as optical information recording media such as CDs, DVDs or MDs.

The substrate is formed of silica glass, a silicone, a polycarbonate, polystyrene or any other synthetic resin moldable or otherwise formable into a disk shape, preferably an injection-moldable synthetic resin. Use of economical synthetic resin substrates can achieve low running cost compared with glass chips which have been used conventionally.

On a front surface 101 of the substrate 1, detecting sections 3, 3, . . . and address pits 103, 103, . . . are spirally recorded by an optical disk mastering technique (see FIG. 1). The detecting sections serve as places of an interaction between a detection substance D and a target substance T, whereas the address pits are used to specify positions on the substrate 1. The length, width and depth of each detecting section 3 are each of from several micrometers to several hundreds micrometers, and their values are determined based on the spot diameter of excitation light P and the possible minimum drop volume of sample solutions (a detection substance containing solution and a target substance containing solution).

Formed on one of the surfaces of the substrate 1 is a reflecting layer 2 the thickness of which is in a range of from several nanometers to several tens nanometers or so. Within the above-described range, the thickness of the reflecting layer 2 can be determined as desired depending on the material which makes up the reflecting layer 2.

When the reflecting layer 2 is formed of a single layer of a metallic material or a single layer of an inorganic material, its reflectance to a laser beam for servo-controlled operations to be mentioned subsequently herein may desirably be set within a range of from 5% to 50% (inclusive), because this range is a suitable range capable of reconciling a higher laser beam reflectance required to perform more stable servo-controlled operations (servo-controlled focusing and servo-controlled tracking) and translucence to excitation light and fluorescence, said translucence being required for the determination of the intensity of the fluorescence. The above-described reflectance range also makes it possible to fully eliminate disturbance to the servo-controlling laser beam reflected on the substrate 1 even when the refractive indexes of the liquid substances D, T existing on the front surface 101 of the substrate are very close to the refractive index of the substrate 1.

The reflecting layer 2 may be replaced by a reflecting film formed of plural inorganic materials applied one over the other in layers and having wavelength selectivity. In this case, it becomes possible to reflect only a laser beam for servo-controlled operations, thereby obviating the concern about losses of excitation light and fluorescence for the determination of the intensity of the fluorescence. Therefore, a reflecting layer 2 the laser beam reflectance of which is higher than 50% (for example, 90% or higher) can be formed without worrying about any effect on the determination of the intensity of fluorescence.

In the above-described light transmitting layer, the detecting sections 3 of the below-described construction are recessedly arranged.

As illustrated in FIG. 2, each detecting section 3 is provided with a reaction region 31 in the form of a well or groove, into which a sample solution S is dropped, for example, through an inkjet printing nozzle (not shown), and a detecting surface 32 formed on a wall defining the reaction region 31. It is to be noted that the detecting sections 3 are not limited to the illustrated shape and can be arranged as many as needed at predetermined positions depending on the purpose.

The detecting surfaces 32 (see FIG. 2) have been subjected to surface treatment to permit immobilization of the detection substance D. Surface treatment suitable for the immobilization of a desired detection substance such as DNA probe has been selected and applied to the detecting surfaces 32 as needed.

The detecting surfaces may be subjected to surface treatment, for example, with a solution of an amino-containing silane coupling agent or a solution of polylysine. In the case of a substrate made of a synthetic resin, its surface can be treated with a solution of an amino-containing silane coupling agent after plasma treatment and DUV (deep UV) irradiation. Further, copper, silver, aluminum or gold may be sputtered onto the surfaces to form films, and on the surfaces of the films, a substance having functional group(s) (active group(s)) such as amino, thiol or carboxyl group(s), cysteamine, streptoavidin or the like can be coated. Further, a linker may be bound beforehand to the detecting surfaces as needed to permit immobilization of a detection substance.

To the detecting sections 3, 3, . . . arranged at predetermined positions on the front surface 101 of the substrate 1, a nucleotide chain such as a DNA probe, a peptide, protein, a lipid, a low molecular-weight substance, a liposome or any other biological substance or the like is immobilized as the detection substance D. Onto the thus-immobilized detection substance D, the sample solution S with the fluorescence-labeled target substance contained therein is dropped such that the detection substance D and the target substance T are caused to interact with each other to prepare a reaction product R.

In FIG. 2, numeral 4 designates a fluorescent dye applied as a marking to the end of the target substance T (a nucleotide chain in the illustrated embodiment). Instead of this fluorescent dye marking, a fluorescent intercalator may be used to detect an interaction such as hybridization.

A description will next be made with reference to FIG. 3. In the bioassay system according to the present invention, fluorescence F, which has been emitted from the fluorescence-labeled target substance T by irradiation of the excitation light (exciting laser beam) P of a specific wavelength onto the reaction product R, is condensed using a lens (condenser lens) 5 arranged on the side of a back surface 102 opposite to the front surface 101 of the substrate 1, said front surface containing the detecting sections 3 arranged therein, and the intensity of the fluorescence F is determined. Designated at numeral 6 in FIG. 2 is a condenser lens arranged in front of a detector 7.

Figure 3:
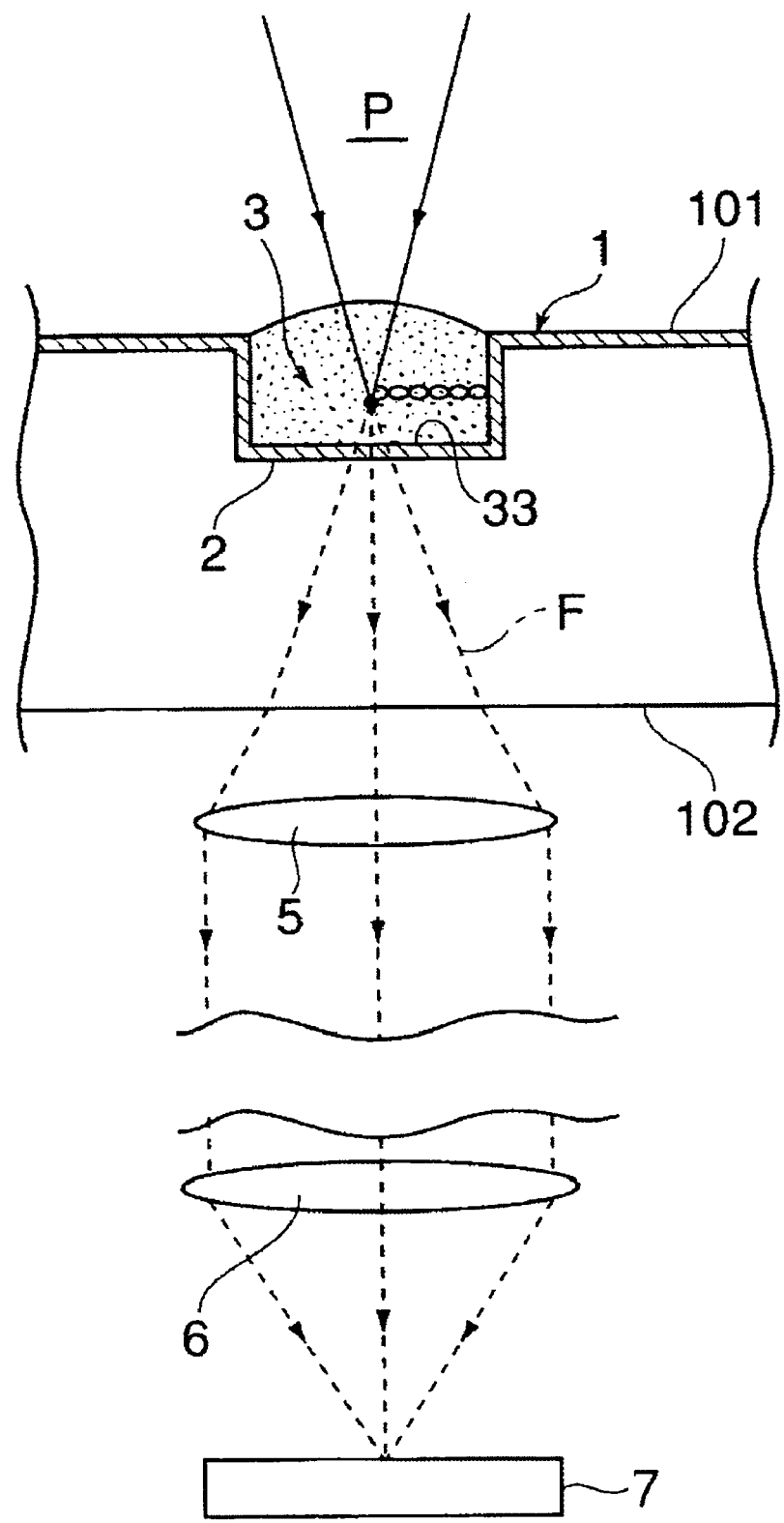
FIG. 3 is a schematic illustration of a state when excitation light (P) is irradiated onto the detecting section (3) from a point above the substrate (1).
Figure 4:
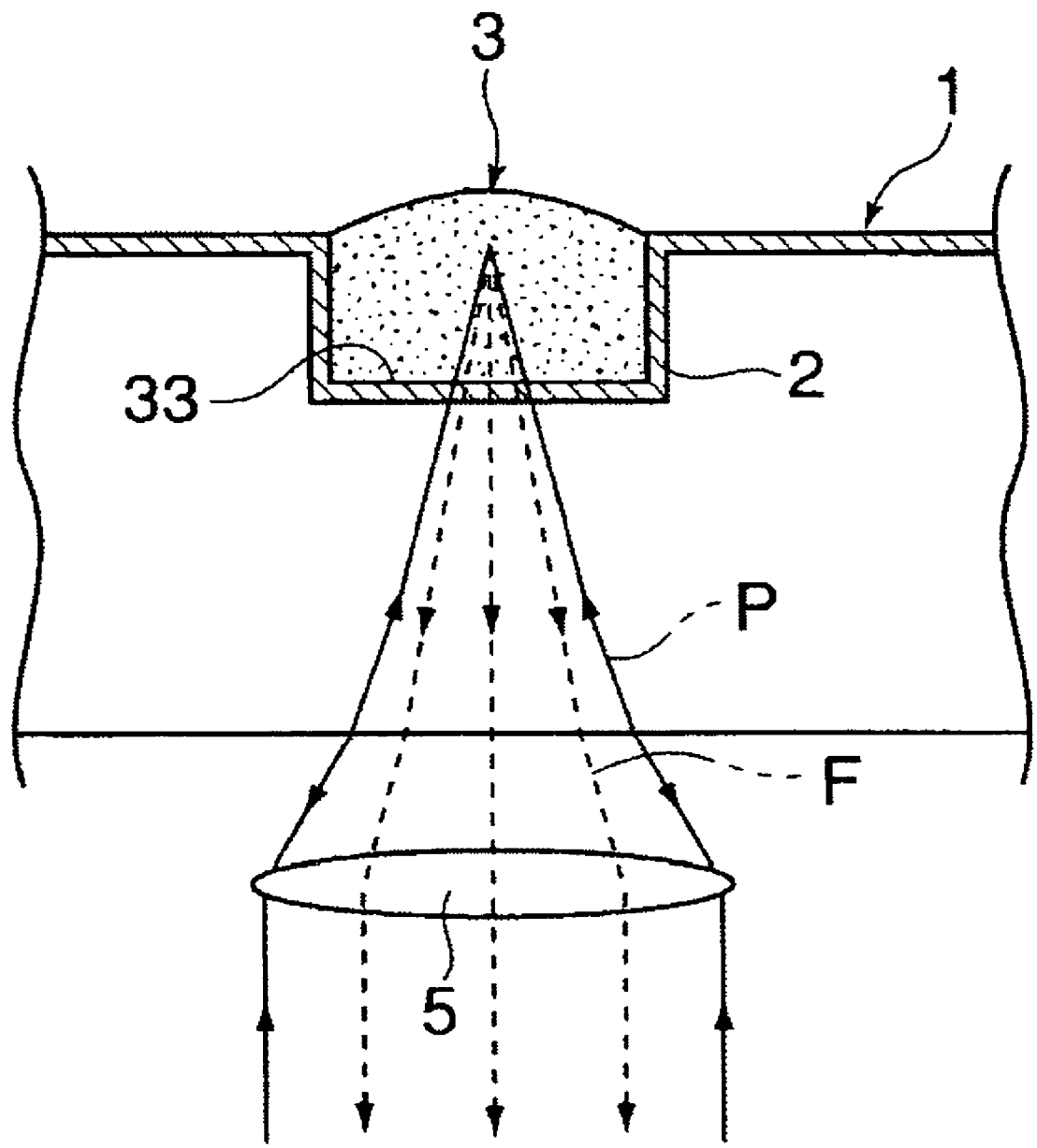
FIG. 4 is a schematic illustration of a state when excitation light (P) is irradiated onto the detecting section (3) from a point below the substrate (1).

The irradiation of the excitation light P is feasible from the direction of either the front surface 101 or the back surface 102 of the substrate 1 (in FIG. 3, an embodiment in which irradiation is effected from the side of the front surface 101 of the substrate is shown). To effectively use the space above the front surface 101 of the substrate as a space for the arrangement of the sample solution dropper and its associated devices, it is preferred to perform the irradiation of the excitation light P from the side of the back surface 102 (see FIG. 4).

In the embodiment that the excitation light P is irradiated onto the detecting section 3 from the side of the front surface (or from the side of the back surface 102) as shown in FIG. 3, the above-described reflecting layer 2 (at least the reflecting layer 2 on a bottom wall 33 of the detecting section 3) is allowed to function as a light transmitting layer having translucence to the fluorescence F and the excitation light P. This makes it possible to irradiate the excitation light P onto the detecting section 3 from the side of the back surface opposite to the front surface 101 of the substrate and also to determine the intensity of the fluorescence F transmitted to the side of the back surface 102 through the light-transmitting layer.

Incidentally, the wavelength of the excitation light P may suitably be in a range of from 400 nm to 700 nm or so, which is coincident with a wavelength range in which general fluorescent substances can be excited.

Based on FIG. 5, a description will hereinafter be made about the overall construction of a suitable embodiment of the bioassay system U according to the present invention.

The substrate 1 of the above-described construction is secured on a spindle 9 arranged extending upwardly from a disk support 8 which is equipped with rotating means. The spindle 9 is fixedly inserted in a center hole 104 (see FIG. 1) of the substrate 1.

The detection substance D and the target substance T, which are to be dropped onto the front surface 101 of the substrate 1, are in the form of solutions. For the avoidance of various problems such as dripping, it is therefore extremely desirous to horizontally hold the substrate 1 onto which the solutions are to be dropped.

Arranged above the substrate 1 are nozzles 10 constructed such that the sample solution S can be dropped into the detecting sections 3, 3, . . . at predetermined positions while accurately tracking them. A control unit designated at numeral 11 controls entire dropping operations by the nozzles 10 on the basis of focus information and tracking information to be mentioned subsequently herein.

The excitation light P is outputted from a laser diode 12. Subsequent to conversion into parallel rays by a collimator lens 6, the parallel rays are refracted 90° by a dichroic mirror 13 and then, refracted 90° by a mirror 14 arranged ahead as viewed in the advancing direction. The parallel rays enter the condenser lens 5 supported on an actuator 15, and are then irradiated onto the detecting section 3 from the side of the back surface 102 of the substrate 1. Incidentally, numeral 16 indicates a signal transmitted from the control unit 11 to control a laser diode driver 17.

Here, the excitation light P is constricted to a size of several micrometers or so on the surface of the substrate by the condenser lens 5. To make effective use of this minute spot diameter of the excitation light, inkjet printing nozzles capable of dropping a solution of picoliter order microvolume are suited as the nozzles 10 for dropping the detection substance containing solution and the target substance containing solution onto the substrate 1.

The inkjet printing nozzles may be provided as many as the number of solutions to be used. As an alternative, each nozzle may be washed once subsequent to dropping of a solution, and may then be used to drop another solution. This manner makes it possible to handle many kinds of solutions by a smaller number of nozzles. Upon dropping the sample solution S (the detection substance containing solution or the target substance containing solution) onto the substrate 1, each desired solution is dropped to a desired address while reading address information, which have been recorded beforehand on the substrate, by using a servo control laser beam V (which will be mentioned subsequently herein).

When the excitation light P is irradiated onto the fluorescence-labeled target substance T still remaining in the detecting section 3 after washing, that is, the target substance T which has undergone an interaction such as hybridization, fluorescence designated by numeral F is emitted, and this fluorescence F then returns to the side of the back surface 102 of the substrate 1 (see FIG. 4 again).

After this fluorescence F is refracted 90° by the mirror 14 arranged below the substrate 1, it travels straight through the dichroic mirror 13 arranged in the advancing direction of the like, and is then refracted 90° by a dichroic mirror 18 arranged further ahead. Subsequently, the fluorescence F enters an upper lens 19 and is condensed there, and is guided into a detector 7. As is appreciated from the foregoing, the dichroic mirror 18 is equipped with property of reflecting the fluorescence F and also with property of exhibiting translucence to the servo control laser beam V to be mentioned subsequently herein.

The fluorescence is expected to be very low in intensity than RF signals or the like for general optical disks. It is, therefore, suitable to adopt as the fluorescence-detecting detector 7 a photomultiplier tube or avalanche photodiode (APD) having very high sensitivity than general photodiodes.

The fluorescence F detected by the detector 7 is converted into a digital signal 28 of a predetermined bit number by an AD converter 20. Such digital signals 28 are used, for example, for an analysis such as preparation of a map in which each address on the substrate 1 is correlated to the intensity of its corresponding emitted fluorescence.

A description will next be made about the construction of the servo control systems.

Firstly, the condenser lens 5 arranged below the substrate 1 is constructed such that it can be driven in a focusing direction (vertical direction) and in a tracking direction (radial direction) by the actuator 15. As this actuator 15, a two-axis voice coil type actuator of the same type as that employed in a pickup for optical disks is suited.

As described above, the substrate 1 is held horizontally, and the condenser lens 5 is arranged vertically below as viewed from the substrate 1. Therefore, the excitation light P and the servo control laser beam V, which is used for the focus servo control and the tracking servo control, are irradiated from the side of the back surface 102 of the substrate 1.

Owing to the adoption of the construction that the servo control laser beam V is irradiated from the side of the back surface 102 of the substrate 1, the servo control laser beam V is reflected back from the back surface 102 of the substrate 1 without being affected at all by the detection substance D and target substance existing in the solutions accommodated in the detecting section 3 of the substrate 1. The reflected beam is, therefore, not disturbed in direction or intensity by these liquid substances even when the substrate 1 is rotated. This construction is hence very suitable. In other words, neither focusing errors nor tracking errors are subjected to disturbance so that the servo control systems can operate stably.

Figure 5:
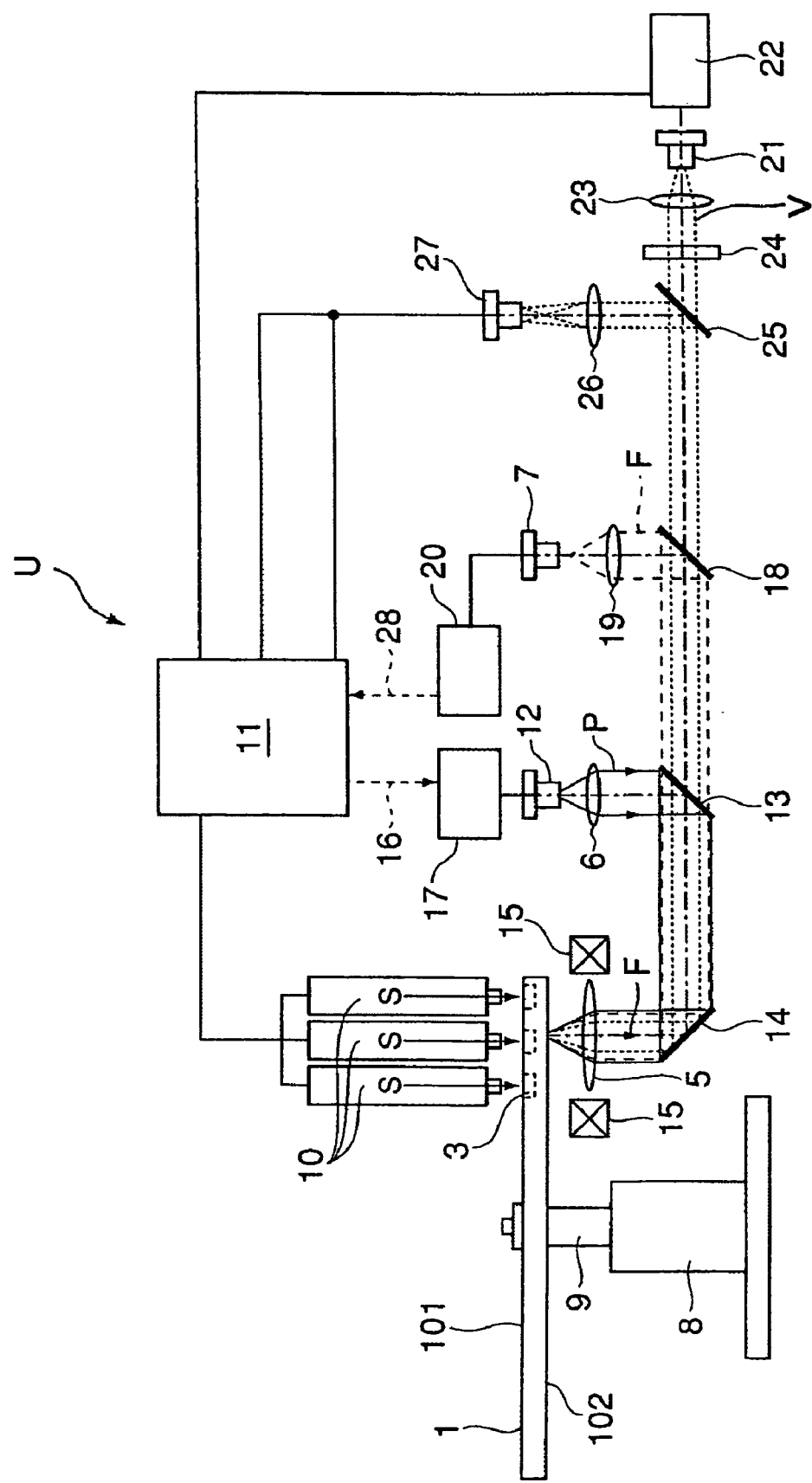
FIG. 5 is a block diagram schematically showing the construction of the bioassay system (U) according to the present invention.

Described specifically, numeral 21 in FIG. 5 designates a servo control laser diode, behind which a driver 22 is arranged to control the diode 21. In the laser emitting direction of the servo control laser diode 21, a collimator lens 23 is arranged. By this lens 23, a servo control laser beam V is converted into parallel rays and is allowed to travel straight.

For the occurrence of focusing errors, several methods may be contemplated including the astigmatic method, the knife edge method and the skew method. In the case of the construction of FIG. 5, the astigmatic method making use of an astigmatism producing lens 26 is adopted.

For the occurrence of tracking errors, on the other hand, the differential push-pull method and the 3-spot method are considered to be appropriate. Both of these methods require obtaining three light spots on the disk. Therefore, as commonly practiced in optical disk pickups, a diffraction grating 24 is inserted in the optical system for the servo control laser, and diffracted $0^{th}$-order and $\pm 1^{st}$-order light beams are irradiated onto the substrate 1 through the condenser lens 5. Incidentally, numeral 27 in FIG. 5 designates a detector for reflected light of the servo control laser. The driver 22 and the detector 27 are controlled by the control unit 11 (see FIG. 5).

It is to be noted that the above-described excitation light P, fluorescence F and laser beam V may be different in wavelength from one another. When a construction is adopted with these lights P, F and V being rendered different in wavelength, the reflecting layer 2 arranged on the substrate 1 is required to have such physical properties that it has translucence (transmittance) of a predetermined degree to the wavelength of the fluorescence F and such a laser beam reflectance as permitting servo controlled operations. In essence, the reflecting layer may have wavelength-dependency in reflectance and transmittance, and may preferably have similar frequency characteristics as low-pass filters. With a single wavelength, it is difficult to improve both of the transmittance of the fluorescence F and the reflectance of the laser beam V. By providing such wavelength dependency, however, it is possible to improve both of the transmittance of the fluorescence F and the reflectance of the laser beam V.

An illustrative bioassay procedure making use of the bioassay system according to the present invention will next be described based on FIG. 6A through FIG. 6E.

Figure 6A:
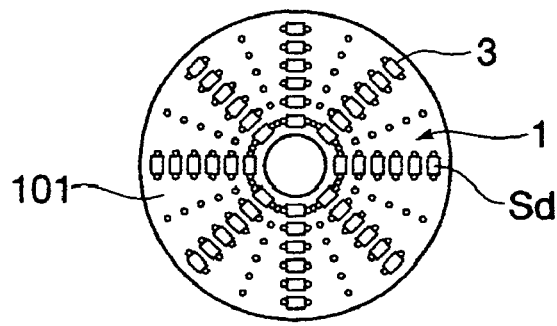
FIG. 6A through FIG. 6E are flow diagrams schematically illustrating a bioassay procedure making use of the system (U).

A substrate 1 is horizontally fixed on the disk support 8 (see FIG. 5). While operating the focus servo control system and the tracking servo control system, the substrate 1 is rotated. While detecting address information, a detection substance containing solution Sd is dropped into predetermined detecting sections through one of the dropping nozzles 10 (see FIG. 5) (FIG. 6A).

Figure 6B:
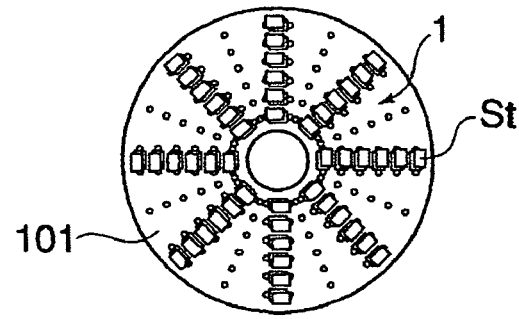

While operating the focus servo control system and the tracking servo control system, the substrate 1 is then rotated. While detecting address information, a solution St containing a fluorescence-labeled target substance is dropped into the predetermined detecting sections through another one of the dropping nozzles 10 (see FIG. 5) (FIG. 6B).

Figure 6C:
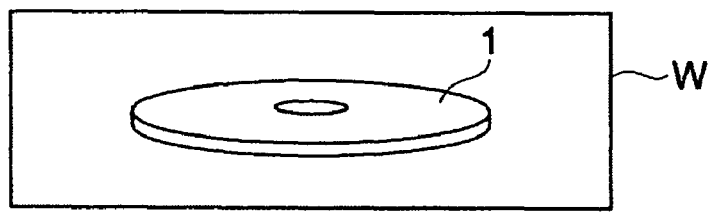

To promote an interaction such as hybridization between the detection substance D and the target substance T, the substrate 1 is then incubated for several hours in a constant-temperature, constant-humidity chamber W (FIG. 6C).

Figure 6D:
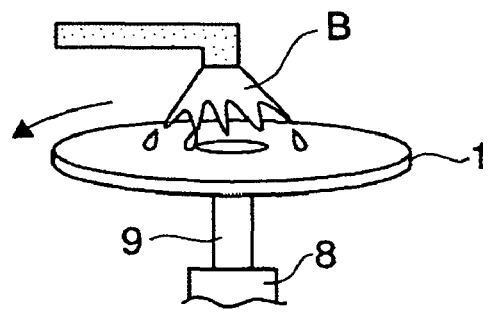

Subsequently, the substrate 1 is washed, for example, with an SSC (saline-sodium citrate) buffer solution B containing SDS as a surfactant to remove the target substance T, which did not exhibit any interaction with the detection substance D immobilized on the substrate 1, from the detecting sections 3 (FIG. 6D).

Figure 6E:
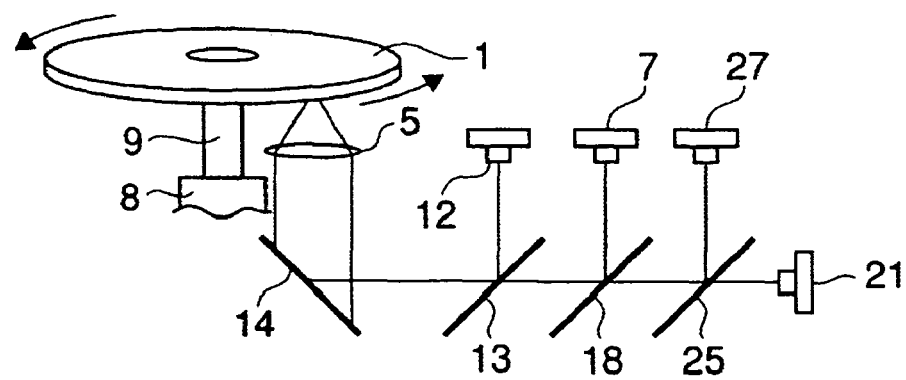

The substrate 1 is fixed again on the disk support 8 such that the front surface 101, on which the detection substance D has been immobilized, is directed upward. While operating the focus control servo system and the tracking control servo system, the substrate 1 is rotated and the excitation light P is irradiated onto the fluorescence-labeled target substance T (the target substance T which exhibited the interaction) (FIG. 6E).

The intensity of fluorescence F emitted from the fluorescent label is detected by the detector to determine the state of interaction between the detection substance D and the target substance T. An output of the detector is converted into the digital signal 28 of the specific bit number by the AD converter 20. In this manner, a map in which each address on the substrate 1 and the intensity of its corresponding fluorescence is prepared.

It should be borne in mind that the bioassay system and bioassay substrate according to the present invention are not limited to the above-described embodiments.

INDUSTRIAL APPLICABILITY

The bioassay system according to the present invention is devised to include means for dropping a solution of a fluorescence-labeled target substance onto a detection substance in a state immobilized on a detecting surface in a reaction region to prepare a reaction product by an interaction between the detection substance and the target substance; and means for irradiating excitation light of a specific wavelength onto the reaction product and condensing fluorescence, which has been emitted from the fluorescence-labeled substance, on a back side of the detecting section to determine an intensity of the fluorescence. Therefore, a wider space can be retained above detecting sections. As a result, it is possible to bring about an advantageous effect that a device for dropping sample solutions into the detecting sections and a group of its associated devices can be arranged with a higher designing tolerance.

According to the present invention, it is also possible to stably and surely perform a series of steps, which include rotating a substrate while actuating a focus servo control system and a tracking servo control system, dropping a detection substance containing solution onto a surface of the substrate to immobilize the detection substance, dropping a fluorescence-labeled target substance onto the immobilized detection substance to subject both of the substances to an interaction such as hybridization, irradiating excitation light onto the substrate, detecting by a detector an intensity of fluorescence emitted as a result, and then analyzing the state of the interaction between the detection substance and the target substance. Further, the operations of the focus servo control system and tracking servo control system are stabilized, thereby making it possible to improve the reliability of measurement results.

The invention claimed is:

1. A bioassay system, comprising:
   means for dropping a solution of a fluorescence-labeled target substance in a reaction region of a bioassay substrate containing a detection substance, the detection substance interacting with the fluorescence-labeled target substance to prepare a reaction product, the bioassay substrate including a wavelength selective layer at a bottom portion of the reaction region, wherein the reaction region is spirally arranged on the bioassay substrate;
   means for condensing fluorescence emitted from the fluorescence-labeled target substance through the wavelength selective layer and a back surface of the reaction region to determine an intensity of the fluorescence, the fluorescence being produced by irradiating excitation light of a first wavelength onto the reaction product; and
   means for controlling the means for dropping the solution based on tracking information of the reaction region and focus information of a control laser beam of a second wavelength irradiated to and reflected from the wavelength selective layer and the back surface of the reaction region, the second wavelength being different from the first wavelength.

2. A bioassay system according to claim 1, wherein the reaction region comprises a detecting section having at least a detection surface, the detection surface being treated to immobilize the detection substance thereon, the detection substance interacting with the fluorescence-labeled target substance when the detection substance is immobilized on the detection surface.

3. A bioassay system according to claim 1, wherein wavelength selective layer is translucent to the fluorescence and the excitation light, and wherein the excitation light is irradiated onto the detection substance through the back surface of the reaction region and through the wavelength selective layer, and the fluorescence is emitted through the back surface of the reaction region and through the wavelength selective layer.

4. A bioassay plate, comprising:
   a detecting section having a reaction region for allowing an interaction between a detection substance and a target substance, wherein the detecting section is optically detectable by a laser beam of a first wavelength, and the reaction region is spirally arranged on the bioassay plate; and
   a wavelength selective layer on a bottom wall of the reaction region, the wavelength selective layer reflecting the laser beam for allowing a control unit to track and focus on the detecting section, and the wavelength selective layer being translucent to excitation light of a second wavelength and fluorescence, the second wavelength being different from the first wavelength.

5. A bioassay plate according to claim 4, wherein the reaction region comprises a detection surface treated to immobilize the detection substance thereon, the detection substance interacting with the fluorescence-labeled target substance when the detection substance is immobilized on the detection surface.

6. A bioassay plate according to claim 4, the bioassay plate being a disk-shaped plate.

7. A bioassay system comprising:
   the bioassay plate according to claim 6;
   a condensing means associated with the bioassay plate, the condensing means comprising a lens arranged on the back surface of the bioassay plate, the lens condensing the laser beam reflected from the wavelength selective layer, thereby obtaining the focus information using the laser beam reflected from the wavelength selective layer;
   a focusing servo control system configured to maintain a distance between the lens and the disk-shaped plate constant using the focus information; and
   a controller for controlling dropping of a solution to the detecting section of the bioassay plate based on the tracking information and the focus information.

8. A bioassay system comprising:
   the bioassay plate according to claim 6;
   a condensing means associated with the bioassay plate, the condensing means comprising a lens arranged on the back surface of the bioassay plate, the lens condensing the laser beam reflected from the wavelength selective layer, thereby obtaining the focus information using the laser beam reflected from the wavelength selective layer;
   a tracking servo control system configured to the lens to precisely track the position of the detection section using the tracking information; and
   a controller for controlling dropping of a solution to the detecting section of the bioassay plate based on the tracking information and the focus information.

9. A bioassay system comprising:
   the bioassay plate of claim 6; and
   a holding means for holding the bioassay plate so that the bioassay plate faces vertically upward.

10. A bioassay system, comprising:
    a nozzle for dropping a fluorescence-labeled substance into a reaction region of a bioassay substrate, the reaction region containing a detection substance, wherein the reaction region is spirally arranged on the bioassay substrate, and the bioassay substrate includes a wavelength selective layer at a bottom portion of the reaction region;
    a controller for controlling the nozzle based on tracking information of the reaction region and focus information of a control laser beam of a first wavelength irradiated to and reflected from the wavelength selective layer and a back surface of the reaction region;
    a light source for irradiating excitation light of a second wavelength onto a reaction product to produce fluorescence, the second wavelength being different from the first wavelength, the reaction product being obtained by causing the detection substance to interact with the fluorescence-labeled substance in the reaction region; and
    a condenser lens for condensing the fluorescence emitted from the reaction product through the wavelength selective layer and the back surface of the reaction region.

11. A bioassay process, comprising:
    controlling a nozzle based on tracking information of a reaction region of a bioassay substrate and focus information of a control laser beam of a first wavelength irradiated to and reflected from a wavelength selective layer and a back surface of the reaction region, wherein the reaction region is spirally arranged on the bioassay substrate, and the wavelength selective layer is formed at a bottom portion of the reaction region;
    dropping a solution of a fluorescence-labeled target substance using the nozzle in a reaction region of the bioassay substrate based on the tracking information and the focus information, the reaction region containing a detection substance, which interacts with the fluorescence-labeled target substance in the reaction region to prepare a reaction product; and condensing fluorescence emitted from the fluorescence-labeled target substance through the wavelength selective layer and the back surface of the reaction region to determine an intensity of the fluorescence, the fluorescence being produced by irradiating excitation light of a second wavelength onto the reaction product, the second wavelength being different from the first wavelength.

12. The bioassay plate of claim 4, wherein the second wavelength ranges from 400 nm to 700 nm.

* * * * *